(12) United States Patent
Joutsamo et al.

(10) Patent No.: US 6,767,909 B2
(45) Date of Patent: Jul. 27, 2004

(54) COMPOUNDS USEFUL FOR TREATMENT OR PREVENTION OF DISEASE MEDIATED BY ALPHA-2B-ADRENOCEPTOR

(75) Inventors: Topi Joutsamo, Turku (FI); Andrei Yurievitch Tauber, Helsinki (FI); Harri Salo, Turku (FI); Anna-Maria Hoffrén, Turku (FI); Siegfreid Wurster, Piikkiö (FI)

(73) Assignee: Oy Juvantia Pharma Ltd., Turku (FI)

( * ) Notice: Subject to any disclaimer, the term of this patent is extended or adjusted under 35 U.S.C. 154(b) by 0 days.

(21) Appl. No.: 10/196,123

(22) Filed: Jul. 17, 2002

(65) Prior Publication Data

US 2003/0073710 A1 Apr. 17, 2003

Related U.S. Application Data

(60) Provisional application No. 60/306,449, filed on Jul. 20, 2001.

(51) Int. Cl.$^7$ .................... C07D 239/42; A61K 31/505; A61K 31/506; A61P 3/04; A61P 9/12
(52) U.S. Cl. .................... 514/256; 514/269; 544/321; 544/330
(58) Field of Search .................... 544/321, 330; 514/256, 269

(56) References Cited

U.S. PATENT DOCUMENTS

| | | | |
|---|---|---|---|
| 5,292,740 A | 3/1994 | Burri et al. | 514/256 |
| 6,150,389 A | 11/2000 | Munk et al. | 514/377 |
| 2002/0058618 A1 | 5/2002 | Wurster et al. | 514/12 |

FOREIGN PATENT DOCUMENTS

WO    WO 01/58454    8/2001

OTHER PUBLICATIONS

McNamara et al., Am. J. Pharmacogenomics, 2(2): 73–78, 2002.*
Fujikura et al., "Studies on Benzenesulfonamide Derivatives With Alpha– and Beta–adrenergic Antagonistic and Antihypertensive Activities," 30 Chem.Pharm.Bull. 4092 (1982)(Abstract).
Michel et al., "Assessment of Imiloxan as a Selective Alpha 2B–adrenoceptor Antagonist," 99 Br. J. Pharmacol. 560 (1990).
Farag et al., "Synthesis of Certain Benzimidazole Derivatives Structurally Related to Antituberculosis Agents," 32 Egypt. J. Pharm Sci. 951 (1991)(Abstract).
Kumar et al., "Synthesis and Biological Activities of Some New S–(Benzimidazol–2–ylmethy)N–substituted Dithiocarbamates and N1–substituted N4–Benzimidazol–2–ylmethyl)Sulfanilamides," 24B Indian J. Chem., Sect. B (1985)(Abstract).

CA Registry, RN 380644–35–9, Benzenesulfonamide, 4-[[(1–methyl–1H–benzimidazol–2–yl)methyl]amino]–N–(4–methyl–2–pyrimidinyl)–.
CA Registry, RN 354563–18–1, Benzenesulfonamide, 4-[[(1–methyl–1H–benzimidazol–2yl)methyl]amino]–N–(4–methyl–2–pyrimidinyl)–.
CA Registry, RN 354563–19–2, Benzenesulfonamide, N–(4,6–dimethyl–2–pyramidinyl)–4 [[(1–methyl–1H–benzimidazol–2–yl)methyl]amino]–.
Varma et al., "Potential Biologically Active Agents. XII. Synthesis and Antibacterial Activity of Substituted p–Methylaminobenzenesulfonamides," J. Indian Chem. Soc., vol. LV, pp. 716–718 (1978).
CAPLUS AN 2001:816614, "Preparation of Nitrophenyl-carboxamide Derivatives as Peroxisome Proliferator–activated Receptor (PPAR) Modulators," WO 01/83427 (Nov. 8, 2001).
STN International Chemcats AN 2002:1405436 "Benzenesulfonamide, 4[1(1–methyl–iH–benzimidazol–2–yl)methyl]–N–(4–methyl–2–pyrimidinyl)–" (Jul. 1, 2001).
STN International CAPLUS, AN 1967:411468, Bedenko et al., "N4–Acylsulfonamides. I. Derivatives of +–(2–ethyoxybenzimido)benzenesulfonamide," 38 Croat. Chem. Acta 309 (1966).
Baumgart et al., 1999, Augmented alpha–adrenergic constriction of atherosclerotic human coronary arteries, Circulation 99:2090–7.
Bloor et al., 1992, Effects of intravenous dexmedetemidine in humans. II. Hemodynamic changes, Anesthesiology 77:1134–42.
Carretero et al., 2000, Essential hypertension. Part I: definition and etiology, Circulation 101(3):329–35.

(List continued on next page.)

*Primary Examiner*—Mukund J. Shah
*Assistant Examiner*—Venkataraman Balasubramanian
(74) *Attorney, Agent, or Firm*—James C. Lydon

(57) ABSTRACT

A compound, suitable as an alpha-2B-adrenoceptor antagoist, having a structure of formula (I)

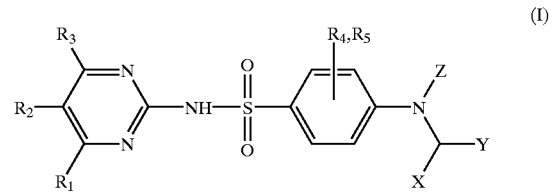

or a pharmaceutically acceptable salt thereof wherein $R_1$, $R_2$, $R_3$, $R_4$ and $R_5$ are independently of each other H, a straight or branched alkyl or alkoxy group with 1 to 4 carbon atoms, or a halogen; X is H, a straight or branched alkyl chain with 1 to 4 carbon atoms, phenyl, —OH or =O; Z is H, acetyl, —CH$_2$—Ph—O—CF$_3$ or —CH$_2$—Ph—CF$_3$, Y is a ring structure optionally linked to formula (I) with an alkyl chain having one or two carbon atoms. The compound is suitable for use in a method for treatment or prevention of a disease mediated by the alpha-2B-adrenoceptor in a mammal.

21 Claims, No Drawings

OTHER PUBLICATIONS

Cocks et al., 1983, Endothelium–dependent relaxation of coronary arteries by noradrenaline and serotonin, Nature 305:627–30.

Duka et al., 2000, Role of the postsynaptic alpha(2)–adrenergic receptor subtypes in catecholamine–induced vasoconstriction, Gen Pharmacol 34:101–6.

Falk et al., 1995, Coronary plaque disruption, Circulation 92:657–71.

Gavras et al., 1989, Salt–induced hypertension: the interactive role of vasopressin and of the sympathetic nervous system, J Hypertens 7:601–6.

Grundy et al., 1999, Assessment of cardiovascular risk by use of multiple–risk–factor assessment equations: A statement for healthcare professionals from the American Heart Association and the American College of Cardiology, Circulation 100:1481–92.

Heinonen et al., 1999, Identification of a three–amino acid deletion in the alpha2B–adrenergic receptor that is associated with reduced basal metabolic acid rate in obese subjects, J Clin Endocrinol Metab 84:2429–33.

Hughes et al., 1988, Size and site–dependent heterogeneity of human vascular responses in vitro, J Hypertens Suppl 6:S173–5.

Indolfi et al., 1992, Role of alpha 2–adrenoceptors in normal and atherosclerotic human coronary circulation, Circulation 86:1116–24.

Jones et al., 1993, Endothelium–dependent relaxation competes with alpha 1– and alpha 2–adrenergic constriction in the canine epicardial coronary microcirculation, Circulation 87:1264–74.

Kaski et al., 1992, Variant angina pectoris. Role of coronary spasm in the development of fixed coronary obstructions, Circulation 85:619–26.

Lafontan et al., 1998, Regulation of fat–cell function by alpha 2–adrenergic receptors, Adv Pharmacol 42:496–8.

Link et al., 1996, Cardiovascular regulation in mice lacking alpha2–adrenergic receptor subtypes b and c, Science 273:803–5.

Makaritsis et al., 1999a, Role of the alpha2B–adrenergic receptor in the development of salt–induced hypertension, Hypertension 33:14–7.

Makaritsis et al., 1999b, Sympathoinhibitory function of the alpha(2A)–adrenergic receptor subtype, Hypertension 34:403–7.

Makaritsis et al., 2000, Role of alpha(2)–adrenergic receptor subtypes in the acute hypertensive response to hypertonic saline infusion in anephric mice, Hypertension 35:609–13.

Marenberg et al., 1994, Genetic susceptibility to death from coronary heart disease in a study of twins, N Engl J Med 330:1041–6.

Nielsen et al., 1989, Postjunctional alpha 2–adrenoceptors mediate vasoconstriction in human subcutaneous resistance vessels, Br J Pharmacol 97:829–34.

Nielsen et al., 1990, Differential distribution of postjunctional alpha 2 adrenoceptors in human omental small arteries, J Cardiovasc Pharmacol 16:34–40.

Nonogaki, 2000, New insights into sympathetic regulation of glucose and fat metabolism, Diabetologia 43:533–49.

Remme, 1998, The sympathetic nervous system and ischaemic heart disease, Eur Heart J 19 Suppl F:F62–71.

Richardson et al., 1989, Influence of plaque configuration and stress distribution of fissuring of coronary atherosclerotic plaques, Lancet 2:941–4.

Rissanen et al., 1979, Aggregation of coronary risk factors in families of men with fatal and non–fatal coronary heart disease, Br Heart J 42:373–80.

Rissanen, 1979a., Familial occurrence of coronary heart disease: effect of age at diagnosis, Am J Cardiol 44(1):60–6.

Rissanen, 1979b, Sudden coronary death and coronary artery disease. A clinicopathologic appraisal, Cardiology 64:289–302.

Rissanen, 1985, Familial occurrence of coronary heart disease according to clinical manifestation, Acta Med Scand 218:355–63.

Ruffolo et al., 1993, Pharmacologic and therapeutic applications of alpha 2–adrenoceptor subtypes, Annu Rev Pharmacol Toxicol 33:243–79.

Savola, 1989, Cardiovascular actions of medetomidine and their reversal by atipamezole, Acta Vet Scand Suppl 85:39–47.

Snapir et al., 2001, An insertion/deletion polymorphism in the alpha2B–adrenergic receptor gene is a novel genetic risk factor for acute coronary events, J Am Coll Cardiol 37:1516–22.

Snapir et al., 2003a, Variation in the alpha2B–adrenoceptor gene as a risk factor for prehospital fatal myocardial infarction and sudden cardiac death, J Am Coll Cardiol 41:190–4.

Snapir et al., 2003b, The insertion/deletion variation in the alpha2B–adrenoceptor does not seem to modify the risk for acute myocardial infarction, but may modify the risk for hypertension in sib–pairs from families with type 2 diabetes, Cardiovasc Diabetol 2:15.

Talke et al., 2001, Clonidine–induced vasoconstriction in awake volunteers, Anesth Analg 93:271–6.

Taylor et al., 2002, Experimental rupture of atherosclerotic lesions increases distal vascular resistance: a limiting factor to the success of infarct angioplasty, Arterioscler Thromb Vasc Biol 22:153–60.

Tesfamariam, 1988, Inhibition of adrenergic vasoconstriction by endothelial cell shear stress, Circ Res 63:720–5.

Wilson, 1994, Established risk factors and coronary artery disease: the Framingham Study, Am J Hypertens 7:7S–12S.

Zdravkovic et al., 2002, Heritability of death from coronary heart disease: a 36–year follow–up of 20 966 Swedish twins, J Intern Med 252:247–54.

* cited by examiner

COMPOUNDS USEFUL FOR TREATMENT OR PREVENTION OF DISEASE MEDIATED BY ALPHA-2B-ADRENOCEPTOR

This application claims priority of U.S. provisional application S.N. 60/306,449, filed Jul. 20, 2001.

The present invention relates to the use of selective alpha-2B-adrenoceptor antagonists for the manufacture of a pharmaceutical preparation useful for the treatment or prevention of diseases mediated by the alpha-2B-adrenoceptor in mammals.

BACKGROUND OF THE INVENTION

The publications and other materials used herein to illuminate the background of the invention, and in particular, cases to provide additional details respecting the practice, are incorporated by reference.

It is known that alpha-2B-adrenoceptors mediate vascular contractions. Therefore, alpha-2B-antagonists are useful in the treatment or prevention of diseases involving vascular contraction. It has also been found that certain individuals have a genetic polymorphism in the alpha-2B-adrenoceptor gene. It has been observed that the alpha-2B-adrenoceptor protein in some subjects has a deletion of 3 glutamates from the glutamic acid repeat element of 12 glutamates (amino acids 297–309), in an acid stretch of 17 amino acids, located in the third intracellular loop of the receptor polypeptide (WO 01/29082; Heinonen et al., 1999).

OBJECTS AND SUMMARY OF THE INVENTION

An object of this invention is to provide compounds useful for the treatment or prevention of a disease mediated by the alpha-2B-adrenoceptor in a mammal.

Thus this invention concerns a novel compound of formula (I)

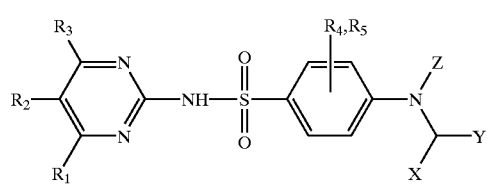

or a pharmaceutically acceptable salt thereof.

$R_1$, $R_2$, $R_3$, $R_4$ and $R_5$ are independently of each other H, a straight or branched alkyl or alkoxy group with 1 to 4 carbon atoms, or a halogen;

X is H, a straight or branched alkyl chain having 1 to 4 carbon atoms, phenyl or —OH;

Z is H, acetyl, —CH$_2$—Ph—O—CF$_3$ or —CH$_2$—Ph—CF$_3$, where Ph is phenyl;

Y is a ring structure optionally linked to formula (I) with an alkyl chain having one or two carbon atoms, wherein the ring structure is
   a) phenyl optionally mono- or disubstituted, wherein each substituent is independently selected from the group consisting of a halogen, a straight or branched alkyl or alkoxy chain with 1 to 4 carbon atoms, a halogen substituted methyl or methoxy group, a nitrile group, an amide group, amino group, or a nitro group;
   b) 2-benzimidazolyl, 2-imidazolyl, or 2- or 3-indolyl, wherein one N optionally has a substituent that is a straight or branched alkyl or alkoxy chain with 1 to 4 carbon atoms, or benzyl; and wherein the 2-benzimidazolyl, 2-imidazolyl, or 2- or 3-indolyl is optionally mono- or disubstituted, wherein each substituent is independently a straight or branched alkyl or alkoxy group with 1 to 4 carbon atoms, or a halogen;
   c) pyridinyl optionally mono- or disubstituted, wherein each substituent is independently a straight or branched alkyl or alkoxy group with 1 to 4 carbon atoms, or a halogen; or
   d) naphthyl optionally mono- or disubstituted, wherein each substituent is independently a straight or branched alkyl or alkoxy group with 1 to 4 carbon atoms, or a halogen;

provided that
   if $R_1$ is methyl; and $R_2$, $R_4$, $R_5$, Z and X is H;
   then Y cannot be an unsubstituted 2-benzimidazolyl if $R_3$ is methyl or H,
   nor can Y be a monosubstituted 2-benzimidazolyl wherein one N has a methyl or ethyl substitution if $R_3$ is methyl.

The following previously known compounds are thus excluded: 4-[(1H-benzimidazol-2-ylmethyl)-amino]-N-(4,6-dimethylpyrimidin-2-yl)-benzenesulfonamide (Kumar & Reddy, 1985), N-(4,6-dimethylpyrimidin-2-yl)-4-[(1-methyl-1H-benzimidazol-2-ylmethyl)-amino]-benzenesulfonamide (No 653716, ChemBridge Corporation, 16981 Via Tazon, Suite G, San Diego, Calif. 92127) and N-(4,6-dimethylpyrimidin-2-yl)-4-[(1-ethyl-1H-benzimidazol-2-ylmethyl)-amino]-benzenesulfonamide (No AE-848/34956037, SPECS and BioSPECS B. V., Fleminglaan 16, 2289 C P Rijswijk, The Netherlands) and N-(4-methyl-2-pyrimidinyl)-4-[(1H-benzimidazol-2-ylmethyl)-amino]-benzenesulfonamide (Farag & El-Mouafi & Khalifa, 1991).

This invention further concerns a method for the treatment or prevention of a disease mediated by the alpha-2B-adrenoceptor in a mammal, comprising administering an alpha-2B-adrenoceptor antagonist to a mammal in need of said treatment, said antagonist comprising a compound of formula (I)

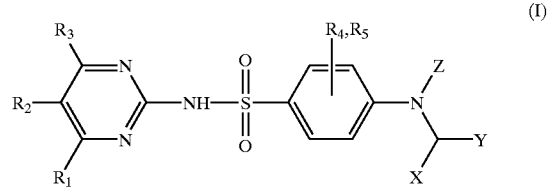

or a pharmaceutically acceptable salt thereof wherein
   $R_1$, $R_2$, $R_3$, $R_4$ and $R_5$ are independently of each other H, a straight or branched alkyl or alkoxy group with 1 to 4 carbon atoms, or a halogen;
   X is H, a straight or branched alkyl chain having 1 to 4 carbon atoms, phenyl, —OH or =O;
   Z is H, acetyl, —CH$_2$—Ph—O—CF$_3$ or —CH$_2$—Ph—CF$_3$, where Ph is phenyl;
   Y is a ring structure optionally linked to formula (I) with an alkyl chain having one or two carbon atoms, wherein the ring structure is
   a) phenyl optionally mono- or disubstitued, wherein each substituent is independently selected from the group consisting of a halogen, a straight or branched alkyl or alkoxy chain with 1 to 4 carbon atoms, a halogen substituted methyl or methoxy group, an acetyl group, a nitrile group, an amide group, an amino group, or a nitro group;

b) 2-benzimidazolyl, 2-imidazolyl, or 2- or 3-indolyl, wherein one N optionally has a substituent that is a straight or branched alkyl or alkoxy chain with 1 to 4 carbon atoms, or benzyl; and wherein the 2-benzimidazolyl, 2-imidazolyl, or 2- or 3-indolyl is optionally mono- or disubstituted, wherein each substituent can independently be a straight or branched alkyl or alkoxy group having 1 to 4 carbon atoms, or a halogen;

(c) pyridinyl optionally mono- or disubstituted, wherein each substituent is independently a straight or branched alkyl or alkoxy group with 1 to 4 carbon atoms, or a halogen; or (d) naphthyl optionally mono- or disubstituted, wherein each substituent is independently a straight or branched alkyl or alkoxy group with 1 to 4 carbon atoms, or a halogen;

provided that if $R_1$ and $R_3$ is methyl; and $R_2$, $R_4$, $R_5$, Z and X is H; then Y cannot be a monosubstituted 2-benzimidazolyl wherein one N has a methyl or ethyl substitution; or if $R_1$ and $R_3$ is methyl; $R_2$, $R_4$, $R_5$ and Z is H and X is =O;

then Y cannot be a monosubstituted phenyl with an ethoxy group in the 4-position.

The following compounds previously known to be selective alpha-2B-adrenoceptor antagonists are thus excluded: N-(4,6-dimethylpyrimidin-2-yl)-4-[(1-methyl-1H-benzimidazol-2-ylmethyl)-amino]-benzenesulfonamide (No 653716, ChemBridge Corporation, 16981 Via Tazon, Suite G, San Diego, Calif. 92127), N-(4,6-dimethylpyrimidin-2-yl)-4-[(1-ethyl-1H-benzimidazol-2-ylmethyl)-amino]-benzenesulfonamide (No AE-848/34956037, SPECS and BioSPECS B. V., Fleminglaan 16, 2289 C P Rijswijk, The Netherlands) and N-[4-(4,6-dimethylpyrimidin-2-ylsulfamoyl)-phenyl]-4-ethoxy-benzamide (No AF-399/36012031, SPECS and BioSPECS B. V., Fleminglaan 16, 2289 C P Rijswijk, The Netherlands).

DETAILED DESCRIPTION OF THE INVENTION

Preferred compounds of the invention are compounds of formula (I)

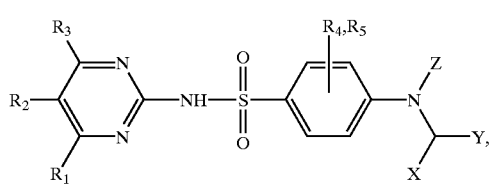

as defined in the preceding summary or pharmaceutically acceptable salts thereof wherein $R_1$ and $R_3$ are methyl and $R_2$, $R_4$ and $R_5$ are H.

In some preferable compounds X is H, Y is a phenyl optionally mono- or disubstituted with a straight or branched alkoxy group and Z is H. Compounds fulfilling all of the aforementioned characteristics and wherein said phenyl is substituted and said alkoxy substituent is methoxy are 4-(2,4-dimethoxybenzylamino)-N-(4,6-dimethylpyrimidin-2-yl)-benzenesulfonamide, N-(4,6-dimethylpyrimidin-2-yl)-4-(3-methoxybenzylamino)-benzenesulfonamide, 4-(3,5-dimethoxybenzylamino)-N-(4,6-dimethylpyrimidin-2-yl)-benzenesulfonamide, 4-(2,5-dimethoxybenzylamino)-N-(4,6-dimethylpyrimidin-2-yl)-benzenesulfonamide and N-(4,6-dimethylpyrimidin-2-yl)-4-(2-methoxybenzylamino)-benzenesulfonamide.

In other preferred compounds X is H, Y is a phenyl optionally mono- or disubstituted with a straight or branched alkyl and/or a halogen and Z is H. These comprise compounds such as 4-benzylamino-N-(4,6-dimethylpyrimidin-2-yl)-benzenesulfonamide, N-(4,6-dimethylpyrimidin-2-yl)-4-(2-methylbenzylamino)-benzenesulfonamide, 4-(2,4-dimethylbenzylamino)-N-(4,6-dimethylpyrimidin-2-yl)-benzenesulfonamide, N-(4,6-dimethylpyrimidin-2-yl)-4-(3-methylbenzylamino)-benzenesulfonamide, N-(4,6-dimethylpyrimidin-2-yl)-4-(4-methylbenzylamino)-benzenesulfonamide, 4-(2,5-dimethylbenzylamino)-N-(4,6-dimethylpyrimidin-2-yl)-benzenesulfonamide, 4-(2,6-dimethylbenzylamino)-N-(4,6-dimethylpyrimidin-2-yl)-benzenesulfonamide, 4-(4-bromobenzylamino)-N-(4,6-dimethylpyrimidin-2-yl)-benzenesulfonamide and 4-(2,6-dichlorobenzylamino)-N-(4,6-dimethylpyrimidin-2-yl)-benzenesulfonamide.

Further preferred compounds are N-(4,6-dimethylpyrimidin-2-yl)-4-[(1-ethyl-1H-indol-3-ylmethyl)-amino]-benzenesulfonamide, N-(4,6-dimethylpyrimidin-2-yl)-4-[(1-isobutyl-1H-benzimidazol-2-ylmethyl)-amino]-benzenesulfonamide, N-(4,6-dimethylpyrimidin-2-yl)-4-(1-phenylethylamino)-benzenesulfonamide, N-(4,6-dimethylpyrimidin-2-yl)-4-[2-(2-methoxyphenyl)-ethyl-amino]-benzenesulfonamide and N-(4,6-dimethylpyrimidin-2-yl)-4-[(naphthalen-2-ylmethyl)-amino]-benzenesulfonamide.

According to one embodiment of the invention the compound is N-(4-methyl-2-pyrimidinyl)-4-[[(1-methyl-1H-benzimidazol-2-yl)-methyl]amino]-benzenesulfonamide. The invention also relates to a method for the treatment or prevention of a disease mediated by the alpha-2B-adrenoceptor in a mammal, comprising administering an alpha-2B-adrenoceptor antagonist to a mammal in need of said treatment, said antagonist comprising a compound of formula (I)

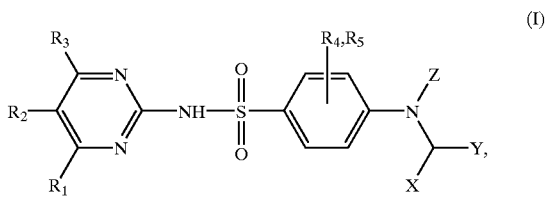

as defined in the preceding summary, or a pharmaceutically acceptable salt thereof.

In many preferable compounds $R_1$ and $R_3$ are typically methyl and $R_2$, $R_4$ and $R_5$ are typically H.

In some preferable compounds X is H, Y is a phenyl optionally mono- or disubstituted with a straight or branched alkoxy group and Z is H. Especially preferable compounds are compounds in which said phenyl is substituted and said alkoxy substituent is methoxy. Such compound comprise 4-(2,4-dimethoxybenzylamino)-N-(4,6-dimethylpyrimidin-2-yl)-benzenesulfonamide, N-(4,6-dimethylpyrimidin-2-yl)-4-(3-methoxybenzylamino)-benzenesulfonamide, 4-(3,5-dimethoxybenzylamino)-N-(4,6-dimethylpyrimidin-2-yl)-benzenesulfonamide, 4-(2,5-dimethoxybenzylamino)-N-(4,6-dimethylpyrimidin-2-yl)-benzenesulfonamide and N-(4,6-dimethylpyrimidin-2-yl)-4-(2-methoxybenzylamino)-benzenesulfonamide.

In other preferable compounds X is H, Y is a phenyl optionally mono- or disubstituted with a straight or branched alkyl and/or a halogen and Z is H. Such compound comprise 4-benzylamino-N-(4,6-dimethylpyrimidin-2-yl)-benzenesulfonamide, N-(4,6-dimethylpyrimidin-2-yl)-4-(2-methylbenzylamino)-benzenesulfonamide, 4-(2,4-dimethylbenzylamino)-N-(4,6-dimethylpyrimidin-2-yl)-benzenesulfonamide, N-(4,6-dimethylpyrimidin-2-yl)-4-(3-methylbenzylamino)-benzenesulfonamide, N-(4,6-dimethylpyrimidin-2-yl)-4-(4-methylbenzylamino)-benzenesulfonamide, 4-(2,5-dimethylbenzylamino)-N-(4,6-dimethylpyrimidin-2-yl)-benzenesulfonamide, 4-(2,6-dimethylbenzylamino)-N-(4,6-dimethylpyrimidin-2-yl)-benzenesulfonamide, 4-(4-bromobenzylamino)-N-(4,6-dimethylpyrimidin-2-yl)-benzenesulfonamide and 4-(2,6-dichlorobenzylamino)-N-(4,6-dimethylpyrimidin-2-yl)-benzenesulfonamide.

Further preferred compounds comprise 4-[(1H-benzimidazol-2-ylmethyl)-amino]-N-(4,6-dimethylpyrimidin-2-yl)-benzenesulfonamide, N-(4,6-dimethylpyrimidin-2-yl)-4-[(1-ethyl-1H-indol-3-ylmethyl)-amino]-benzenesulfonamide, N-(4,6-dimethylpyrimidin-2-yl)-4-[(1-isobutyl-1H-benzimidazol-2-yl-methyl)-amino]-benzenesulfonamide, N-(4,6-dimethylpyrimidin-2-yl)-4-(1-phenylethylamino)-benzenesulfonamide, N-(4,6-dimethylpyrimidin-2-yl)-4-[2-(2-methoxyphenyl)-ethylamino]-benzenesulfonamide and N-(4,6-dimethylpyrimidin-2-yl)-4-[(naphthalen-2-ylmethyl)-amino]-benzenesulfonamide.

Alpha-2B-adrenoceptor antagonists are useful in the treatment and/or prevention of many diseases.

Individuals having a deletion in the alpha-2B-adrenoceptor protein (WO 01/29082; Heinonen et al., 1999), particularly the deletion/deletion genotype (D/D genotype) is an important target group, which benefits from administration of selective alpha-2B-adrenoceptor antagonists. These individuals have a deletion of 3 glutamates from the glutamic acid repeat element of 12 glutamates (amino acids 297–309), in an acid stretch of 17 amino acids, located in the third intracellular loop of the receptor polypeptide.

It has been found that in a population-based cohort of Finnish middle-aged men that subjects with a D/D genotype of the alpha-2B-adrenoceptor gene have a significantly elevated risk for acute myocardial infarction (AMI) in a five-year follow-up study. The risk for AMI was increased in subjects who had no previously diagnosed coronary heart disease (CHD) at the study outset. Therefore, it has been postulated that the D/D genotype is related to an impaired capacity to down-regulate alpha-2B-adrenoceptor function during sustained receptor activation. Therefore, alpha-2B-adrenoceptors are believed to be involved in the pathogenesis of a significant fraction of all cases of AMI, especially in subjects with the D/D genotype, but also in I/D and I/I subjects (I means "insertion" and stands for the "normal" allele).

The alpha-2B-adrenoceptor antagonists as disclosed in this invention would be particularly useful in the treatment or prevention of coronary heart diseases. As examples can be mentioned a) Acute AMI If alpha-2B-adrenoceptor dependent vasoconstriction is a causative factor in some cases of AMI, then antagonism of these receptors should restore coronary circulation and reduce the ischemic myocardial damage.

b) Unstable Angina Pectoris

An alpha-2B-adrenoceptor antagonist will relieve the vasoconstrictive component in the sustained ischemic episode, thus alleviating the symptoms and preventing AMI.

c) Prinzmetal's Variant Form of Angina Pectoris

Vasoconstriction is a key factor in the pathogenesis of Prinzmetal's angina, and an alpha-2B-adrenoceptor antagonist may resolve and prevent attacks.

d) Other Forms of Chronic Angina Pectoris and CHD

An alpha-2B-adrenoceptor antagonist will help to alleviate the vasoconstrictive component in all types of CHD, providing both symptomatic relief and protection from AMI. A general reduction in vascular tone will contribute to this by reducing venous return, cardiac workload and oxygen consumption (a nitrate-type effect; see below).

e) Prevention of Restenosis after Coronary Angioplasty in Cases where Vasoconstriction Plays a Role in Restenosis Furthermore, the alpha-2B-adrenoceptor antagonists as disclosed in this invention would be useful in the treatment or prevention of essential hypertension, especially in subjects with increased sympathetic activity and a hyperdynamic circulatory system.

In the study mentioned above, the D/D variant of the alpha-2B-adrenoceptor gene was not clearly associated with blood pressure. The inventors believe that this was due to two main factors, 1) antihypertensive treatment, and 2) complex regulation of systemic blood pressure. In another study (Heinonen et al.), it was observed that the D/D genotype was associated with reduced basal metabolic rate and reduced heart rate. These associations probably reflect increased vascular resistance in these subjects.

In transgenic mice with targeted inactivation of the alpha-2B-adrenoceptor gene, intravenously administered alpha-2-adrenoceptor agonists fail to induce the characteristic blood pressure elevation, which is seen in normal animals and also in humans after large doses of such drugs (Link et al., 1996). The hypotensive effect of these drugs was markedly accentuated. This demonstrates that alpha-2B-adrenoceptors mediate vascular contraction. Thus, an antagonist should reduce blood pressure. This effect has not been seen with alpha-2B-non-selective alpha-2-adrenoceptor antagonists, because antagonism of alpha-2A-adrenoceptors increases sympathetic outflow, cardiac output and blood pressure. In mice with dysfunctional alpha-2A-adrenoceptors, alpha-2-adrenoceptor agonists caused an accentuated hypertensive response and no hypotension (MacMillan et al., 1996).

An alpha-2B-adrenoceptor antagonist is postulated to have favourable effects in hypertensive subjects through their effects on renal function, muscle blood flow, and also on vascular resistance in other vascular beds. The anti-AMI effect of such a drug will be an additional benefit, as hypertension is a significant risk factor for AMI. This protection is due to three factors: 1) a reduction in systemic blood pressure, 2) decreased risk of coronary vasoconstriction, and 3) a nitrate-like effect on venous return, myocardial workload and oxygen consumption.

Moreover, the alpha-2B-adrenoceptor antagonists as disclosed in this invention would be useful in the treatment or prevention of other vascular diseases. Specifically, benefits can be expected in the treatment or prevention of vasoconstriction and hypoxic brain damage subsequent to subarachnoid haemorrhage, migraine, Raynaud's disease and cold intolerance, pre-eclampsia, male erectile dysfunction, and obesity and the metabolic syndrome.

The last mentioned effect is due to the fact that reduced muscle blood flow and reduced basal metabolic rate contribute to the development of obesity and hypertension. An alpha-2B-adrenoceptor antagonist will, by increasing the muscle blood flow, increase energy expenditure and shift the caloric balance to a favourable direction.

The alpha-2B-adrenoceptor antagonists disclosed in this invention are also useful in anaesthesia and analgesia to potentiate the clinical efficacy of alpha-2-adrenoceptor agonists, which are not selective for the alpha-2B-adrenoceptor subtype. By blocking the vasoconstriction induced by these agonists, a simultaneously administered alpha-2B-adrenoceptor antagonist will allow the use of larger doses of said agonists, up to anaesthetic dose levels which have not previously been possible in man, only in veterinary anaesthetic practice.

TABLE 1

Human $\alpha_2$-adrenoceptor subtypes binding affinities. Data is presented as Ki's in nM (Mean ± SEM).

| Compound | alpha-2A | alpha-2B | alpha-2C |
|---|---|---|---|
| A | >13000 | 160 ± 20 | >30000 |
| B | >4500 | 34 ± 2 | >10000 |
| C | 2000 ± 400 | 10 ± 2 | >10000 |
| D | >10000 | 440 ± 70 | >10000 |
| E | >5100 | 20 ± 4 | >10000 |
| F | >4300 | 43 ± 7 | >10000 |
| G | 2200 ± 600 | 32 ± 5 | >10000 |
| H | >30000 | 8000 ± 500 | >30000 |

Results expressed in the form of ">" means that no numerical values for Ki's could be established due to lack of displacement or due to incomplete competition curves. However, the experimental data indicated that, at a minimum, the Ki's must be larger than the numbers given.

Antagonist Activity on Human Alpha-2-adrenoceptor Subtypes

Antagonist potencies were determined as the ability of test compounds to competitively inhibit epinephrine-stimulated $^{35}$S-GTPγS binding to G proteins (Tian et al., 1993; Wieland and Jakobs, 1994; Jasper et al., 1998) in membranes of CHO cells stably transfected with one of the three human $\alpha_2$ subtypes (Pohjanoksa et al., 1997; Marjamäki et al., 1998). Membranes (2-6 µg of protein per sample) and 12 concentrations of test compound were preincubated for 30 min with a fixed concentration fo epinephrine (5 µM for $\alpha_{2A}$, 15 µM for $\alpha_{2B}$, 5 µM for $\alpha_{2C}$) in 50 mM Tris, 5 mM MgCl$_2$, 150 mM NaCl, 1 mM DTT, 1 mM EDTA, 10 µM GDP, 30 µM ascorbic acid, pH 7.4 at room temperature. Binding of radiolabel was started by the addition of trace amounts of $^{35}$S-GTPγS (0.08–0.15 nM, specific activity 1250 Ci/mmol)

EXPERIMENTAL SECTION

Human Alpha-2-adrenoceptor Binding Affinity

The affinity of test compounds for the three human ($\alpha_2$-adrenoceptor subtypes ($\alpha_{2A}$, $\alpha_{2B}$ and $\alpha_{2C}$) was determined in competition binding assays with $^3$H-rauwolscine. The biological material for these experiments consisted of membranes from Shionogi S115 cells stably transfected with any of the three human $\alpha_2$ subtypes (Marjamäki et al. 1992). Membrane (5–10 µg of total protein per sample) and 1–2 nM $^3$H-rauwolscine (specific activity 78 Ci/mmol) were incubated in 50 mM KH$_2$PO$_4$, pH 7.5 with 6 concentrations of the compounds. Each concentration was run in duplicate. Non-specific binding was defined by 100 µM oxymetazoline and corresponded to 5–15% of total binding. After 30 min at room temperature, incubations were terminated by rapid vacuum filtration through GF/B glass fiber filter and three 5 ml washes with ice-cold incubation buffer. The filters were then dried, impregnated with scintillate and their radioactivity was measured by scintillation counting. The analysis of the experiments was carried out by non-linear least square curve fitting. Experimentally determined IC50 values were converted to Ki's by making use of the Cheng-Prusoff equation (Cheng and Prusoff, 1973). Experiments were repeated a minimum of three times. to the incubation mixture. After an additional 60 min at room temperature, the incubation was terminated by rapid vacuum filtration through glass fibre filter. Filters were washed three times with 5 ml ice cold wash buffer (20 mM Tris, 5 mM MgCl$_2$, 1 mM EDTA pH 7.4 at room temperature), dried and counted for radioactivity in a scintiallation counter. Analysis of experiments was carried out by non-linear least square fitting. Results are based on a minimum of three experiments.

TABLE 2

Antagonist effect on human $\alpha_2$-adrenoceptor subtypes. Data is presented as KB's in nM (Mean ± SEM).

| Compound | alpha-2A | alpha-2B | alpha-2C |
|---|---|---|---|
| B | 14500 ± 3600 | 75 ± 9 | 5700 ± 700 |
| C | 5400 ± 1400 | 17 ± 5 | 6300 ± 1400 |
| E | 7900 ± 3100 | 29 ± 5 | 7300 ± 1100 |
| F | 8700 ± 1100 | 240 ± 60 | 12000 ± 2000 |
| G | 3200 ± 500 | 86 ± 64 | 4700 ± 1800 |

For the purpose of the invention, the alpha-2B-adrenoceptor antagonist or its pharmaceutically acceptable salt can be administered by various routes. The suitable administration forms include, for example, oral formulations; parenteral injections including intravenous, intramuscular, intradermal and subcutanous injections; transdermal or rectal administration forms. The required dosage of the compounds of the alpha-2B-adrenoceptor antagonist will vary with the particular condition being treated, the severity of the condition, the duration of the treatment, the administration route and the specific compound being employed. The suitable dose varies in the range 5 µg to 100 mg per kg body weight and day for an adult person.

EXAMPLES

Example 1
N-(4,6-Dimethylpyrimidin-2-yl)-4-[(1-ethyl-1H-benzimidazol-2-ylmethyl)-amino]-benzenesulfonamide
Step I: Alkylation of 2-hydroxymethylbenzimidazole 99.2 mg (0.67 mmol) 2-hydroxymethylbenzimidazole was dissolved in 3 ml methanol. Potassium carbonate (103.1 g, 0.75 mmol) and diethylsulfate (442 µl 3.38 mmol) were added to the reaction mixture. Solution was stirred and refluxed overnight. The reaction mixture was then evaporated to dryness and purified on silica using gradient elution (chloroform to 5% methanol in chloroform) to obtain white crystals of 1-ethyl-2-hydroxymethylbenzimidazole, 41 mg (32%).

Step II: Chlorination of 1-ethyl-2-hydroxymethylbenzimidazole 20 mg (0.11 mmol) 1-ethyl-2-hydroxymethylbenzimidazole was dissolved in 2 ml dichloromethane. Thionyl chloride (24 µl, 0.33 mmol) was diluted 20 times with dichloromethane and the solution was added to the reaction mixture. Reaction mixture was stirred at room temperature for two hours, evaporated to dryness and washed with water to yield 1-ethyl-2-chloromethylbenzimidazole as pale yellow crystals, 36 mg (95%).

Step III: Coupling Reaction between 1-ethyl-2-chloromethylbenzimidazole and Sulfamethazine 32.4 mg (0,12 mmol) sulfamethazine and 36 mg (0.18 mmol) 1-ethyl-2-chloromethylbenzimidazole were dissolved in 4 ml methanol. 64 µl (0.44 mmol) triethylamine and catalytic amount of sodium iodide were added to the reaction mixture. Solution was stirred and refluxed overnight. The reaction mixture was then evaporated to dryness, and purified on silica using gradient elution (chloroform to 5% methanol in chloroform) to provide white crystals of the title compound, 10 mg (20%). $^1$H NMR (DMSO-$d_6$, 500 MHz): 7.68 (2H, m), 7.60 (1H, m), 7.52 (1H, m), 7.22 (1H, m), 7.17 (1H, m), 7.00 (1H, br, s), 6.78 (3H, m), 6.60 (1H, br, s), 4.60 (2H, m), 4.30 (2H, q, 7.2 Hz), 2.18 (6H, s), 1.28 (3H, t, 7.2 Hz); MS (ESI$^+$): m/z 437 (M+H)$^+$.

Example 2

4-[(1H-Benzimidazol-2-ylmethyl)-amino]-N-(4,6-dimethylpyrimidin-2-yl)-benzenesulfonamide Following the procedure outlined in Step III of example 1, but without triethylamine and substituting 1-ethyl-2-chloromethylbenzimidazole by 2-chloromethylbenzimidazole afforded the title compound with the yield of 51%. $^1$H NMR (DMSO-$d_6$, 500 MHz): 7.70 (2H, m), 7.48 (2H, br, m), 7.13 (2H, m), 7.11 (1H, t, 5.8 Hz), 6.70 (3H, m), 4.52 (2H, d, 5.8 Hz), 2.21 (6H, s); MS (ESI$^+$): m/z 409 (M+H)$^+$.

Example 3

N-(4,6-Dimethylpyrimidin-2yl)-4-[(pyridin-4-ylmethyl)-amino]-benzenesulfonamide

Following the procedure outlined in Step III of example 1 without triethylamine and substituting 1-ethyl-2-chloromethylbenzimidazole by 4-picolylchloride hydrochloride afforded the title compound with the yield of 54%. MS (ESI$^+$): m/z 392 (M+Na)$^+$, 370 (M+H)$^+$.

Example 4

N-(4,6-Dimethylpyrimidin-2-yl)-4-[(1-isobutyl-1H-benzimidazol-2-ylmethyl)-amino]-benzenesulfonamide (Compound A)

Following the procedure outlined in example 1, but substituting in step I ethyl bromide for isobutyl iodide, afforded the title compound with stepwise yields of 15%, 95% and 15%. $^1$H NMR (DMSO-$d_6$, 500 MHz): 7.76 (2H, m), 7.70 (1H, m), 7.60 (1H, m), 7.27 (1H, m), 7.22 (1H, m), 7.15 (1H, br, t, 5.3 Hz), 6.86 (2H, m), 6.77 (1H, s), 4.65 (2H, d, 5.3 Hz), 4.13 (2H, d, 7.5 Hz), 2.27 (6H, s), 2.25 (1H, m), 0.91 (6H, d, 6.7 Hz); MS (ESI$^+$): m/z 487 (M+Na)$^+$, 465 (M+H)$^+$.

Example 5

4-[(1-Benzyl-1H-benzimidazol-2-ylmethyl)-amino]-N-(4,6-dimethylpyrimidin-2-yl)-benzenesulfonamide Following the procedure outlined in example 1, but substituting in step I ethyl bromide for benzyl bromide, afforded the title compound with stepwise yields of 23%, 90% and 18%. $^1$H NMR (DMSO$d_6$, 500 MHz): 7.81 (2H, m), 7.52 (1H, m), 7.45 (1H, m), 7.30 (5H, m), 7.16 (2H, m), 6.75 (1H, s), 6.54 (2H, m), 6.02 (1H, br, s), 5.66 (2H, s), 5.63 (2H, s), 2.21 (6H, s); MS (ESI$^+$): m/z 521 (M+Na)$^+$, 499 (M+H)$^+$.

Example 6

4-[(1-Ethyl-1H-benzimidazol-2-ylmethyl)-amino]-N-(5-methoxypyrimidin-2-yl]-benzenesulfonamide Following the procedure outlined in example 1 step III, but substituting sulfamethazine by 5-methoxysulfadiazifle, afforded the title compound with the yield of 8%. Dimethylformaiflide was used as a solvent and additional silica gel chromatography purification with 2:1 petrol ether:ethylacetate was needed. MS (ESI$^+$): m/z 461 (M+Na)$^+$, 439(M+H)$^+$.

Example 7

4-[(1H-Benzimidazol-2-ylmethyl)-amino]-N-(pyrimidin-2-yl)-benzenesulfonamide 628 mg (3.8 mmol) sulfadiazine and 728 mg (3.0 mmol) 2-chloromethylbenzimidazole were dissolved in 10 ml 1 M NaOH. Solution was stirred and refluxed for four hours. Reaction mixture was neutralised with addition of 1 M acetic acid until product precipitated. Crystals were filtered and purified on silica using gradient elution (chloroform to 5% methanol in chloroform) to obtain the title compound as white crystals with 38% yield. $^1$H NMR (DMSO-$d_6$, 500 MHz): 8.46 (2H, m), 7.70 (2H, m) 7.49 (2H, br, m), 7.14 (1H, t, 5.7 Hz) 7.13 (2H, m), 6.98 (1H, m), 6.72 (2H, m), 4.53 (2H, 5.7 Hz); MS (ESI$^+$): m/z 381 (M+H)$^+$.

Example 8

N-(1H-Benzimidazol-2-ylmethyl)-N-[4-(4,6-dimethylpyrimidin-2-ylsulfamoyl)-phenyl]-acetamide 18 mg (0.044 mmol) 4-[(1H-benzimidazol-2-ylmethyl)-amino]-N-(4,6-dimethylpyrimidin-2-yl)-benzenesulfonamide was dissolved in 2 ml of 15% pyridine in dichloromethane. Acetyl chloride (31 µl, 0.44 mmol) was diluted with 1 ml dichloromethane and solution was added to the reaction mixture. After three hours reaction mixture was washed with acidic water and organic layer was evaporated to dryness. Crystals were purified on silica using gradient elution (chloroform to 5% methanol in chloroform) to obtain white crystals with 30% yield. $^1$H NMR (DMSO-$d_6$, 500 MHz): 7.97 (2H, m), 7.60 (2H, m), 7.48 (2H, m), 7.14 (2H, m), 6.68 (1H, s), 5.08 (2H, s), 2.18 (6H, s), 1.93 (3H, s); MS (ESI$^+$): m/z 473 (M+Na)$^+$, 451 (M+H)$^+$.

Example 9

N-(1-Acetyl-1H-benzimidazol-2-ylmethyl)-N-[4-(4,6-dimethylpyrimidin-2-ylsulfamoyl)-phenyl]-acetamide Title compound was purified from the reaction mixture produced according to example 8 with a yield of 14%. $^1$H NMR (DMSO-$d_6$, 500 MHz): 8.15 (2H, m), 7.80 (2H, m), 7.55 (2H, m), 7.48 (1H, s), 7.21 (3H, m), 5.17 (2H, s), 2.54 (6H, s), 2.03 (3H, s), 1.83 (3H, s); MS (ESI$^+$): m/z 493 (M+H)$^+$.

Example 10

4-[(1-Acetyl-1H-benzimidazol-2-ylmethyl)-amino]-N-(4,6-dimethylpyrimidin-2-yl)-benzenesulfonamide Following the procedure of example 8, but instead of 15% pyridine in dichloromethane only few drops of pyridine in dichloromethane were used as a solvent. Method afforded the title compound with a yield similar to that for N-(1H-benzimidazol-2-ylmethyl)-N-[4-(4,6-dimethylpyrimidin-2-ylsulfamoyl)-phenyl]-acetamide. MS (ESI$^+$): m/z 451 (M+H)$^+$.

Example 11

4-Benzylamino-N-(4,6-dimethylpyrimidin-2-yl)-benzenesulfonamide 100 mg (0.36 mmol) sulfamethazine and 70.8 µl (0.60 mmol) benzyl bromide were dissolved in 4 ml methanol. Caesium carbonate (113.4 mg, 0.35 mmol) was added and solution was refluxed overnight with stirring. The reaction mixture was then evaporated to dryness, and purified on silica using gradient elution (chloroform to 2% methanol in chloroform) to obtain white crystals in a yield similar to that described in example 1 for step III. $^1$H NMR (CDCl$_3$, 500 MHz): 7.93 (2H, m), 7.31 (5H, m), 6.58 (3H, m), 4.36 (2H, s), 2.34 (6H, s); MS (ESI$^+$): m/z 369 (M+H)$^+$.

Example 12
4-(4-Bromobenzylamino)-N-(4,6-dimethylpyrimidin-2-yl)-benzenesulfonamide Following the procedure outlined in example 11, but substituting benzyl bromide by 4-bromobenzyl bromide, afforded the title compound with a yield of 8%. $^1$H NMR (CDCl$_3$, 500 MHz): 7.91 (2H, m), 7.45 (2H, m), 7.19 (2H, m), 6.59 (1H, s) 6.55 (2H, m), 4.32 (2H, s), 2.34 (6H, s); MS (ESI$^+$): m/z 469 (M+Na)$^+$, 447 (M+H)$^+$.

Example 13
N-(4,6-Dimethylpyrimidin-2-yl)-4-(2-methylbenzylamino)-benzenesulfonamide (Compound B)

Following the procedure outlined in example 11, but substituting benzyl bromide by 2-methylbenzyl bromide, afforded the title compound in a yield similar to that described in example 1 for step III. $^1$H NMR (CDCl$_3$, 500 MHz): 7.95 (2H, m), 7.22 (4H, m), 6.58 (3H, m), 4.30 (2H, s), 2.35 (3H, s), 2.34 (6H, s); MS (ESI$^+$): m/z 405 (M+Na)$^+$.

Example 14
N-(4,6-Dimethylpyrimidin-2-yl)-4-(4-methylbenzylamino)-benzenesulfonamide Following the procedure outlined in example 11, but substituting benzyl bromide by 4-methylbenzyl bromide, afforded the title compound in a yield similar to that described in example 1 for step III. $^1$H NMR (CDCl$_3$, 500 MHz): 7.92 (2H, m), 7.20 (2H, m), 7.15 (2H, m), 6.58 (3H, m), 4.31 (2H, s), 2.34 (3H, s), 2.33 (6H, s); MS (ESI$^+$): m/z 405 (M+Na)$^+$, 383 (M+H)$^+$.

Example 15
N-(4,6-Dimethylpyrimidin-2-yl)-4-(1-phenylethylamino)-benzenesulfonamide Following the procedure outlined in example 11, but substituting benzyl bromide by (1-bromoethyl)-benzene, afforded the title compound with a yield of 12%. $^1$H NMR (CDCl$_3$, 500 MHz): 7.84(2H, m), 7.31(5H, m), 6.57 (1H, s), 6.46 (2H, m), 4.53 (1H, q, 6.7 Hz), 2.30 (6H, s), 1.54 (3H, d, 6.7 Hz); MS (ESI$^+$): m/z 405 (M+Na)$^+$, 383 (M+H)$^+$.

Example 16
N-(4,6-Dimethylpyrimidin-2yl)-4-(2-methoxybenzylamino)-benzenesulfonamide Following the procedure outlined in example 11, but substituting benzyl bromide by 2-methoxybenzyl bromide, afforded the title compound in a yield similar to that described in example 1 for step III. $^1$H NMR (CDCl$_3$, 500 MHz): 7.92 (2H, m), 7.25 (2H, m), 6.90 (2H, m), 6.59 (3H, m), 4.36 (2H, s), 3.86 (3H, s), 2.32 (6H, s); MS (ESI$^+$): m/z 421 (M+Na)$^+$, 399 (M+H)$^+$.

Example 17
4-(2,4-Dimethylbenzylamino)-N-(4,6dimethylpyrimidin-2-yl)-benzenesulfonamide Following the procedure outlined in example 11, but substituting benzyl bromide by 2,4-dimethylbenzyl bromide, afforded the title compound with a yield of 23%. $^1$H NMR (CDCl$_3$, 500 MHz): 7.94 (2H, m), 7.14 (1H, m), 7.03 (1H, s), 6.98 (1H, m), 6.58 (3H, m), 4.26 (2H, s), 2.34 (6H, s), 2.31 (3H, s), 2.30 (3H, s); MS (ESI$^+$): m/z 419 (M+Na)$^+$, 397 (M+H)$^+$.

Example 18
N-(4,6-Dimethylpyrimidin-2-yl)-4-(3-methylbenzylamino)-benzenesulfonamide Following the procedure outlined in example 11, but substituting benzyl bromide by 3-methylbenzyl bromide, afforded the title compound with a yield of 10%. $^1$H NMR (CDCl$_3$, 500 MHz): 7.93 (2H, m), 7.23 (1H, m), 7.11 (3H, m), 6.62 (1H, s), 6.58 (2H, m), 4.31 (2H, s), 2.36 (6H, s), 2.34 (3H, s); MS (ESI$^+$): m/z 405 (M+Na)$^+$, 383 (M+H)$^+$.

Example 19
4-(2,6Dichlorobenzylamino)-N-(4,6-dimethylpyrimidin-2-yl)-benzenesulfonamide (Compound C)

Following the procedure outlined in example 11, but substituting benzyl bromide by 2,6-dichlorobenzyl bromide, afforded the title compound with the yield of 10%. $^1$H NMR (CDCl$_3$, 500 MHz): 7.96 (2H, m), 7.34 (2H, m), 7.20 (1H, m), 6.71 (2H, m), 6.59 (1H, s), 4.63 (2H, s), 2.34 (6H, s); MS (ESI$^+$): 437 (M+H)$^+$.

Example 20
N-(4,6-Dimethylpyrimidin-2-yl)-4-[(naphthalen-2-ylmethyl)-amino]-benzenesulfonamide (Compound D)

Following the procedure outlined in example 11, but substituting benzyl bromide by 2-bromomethylnaphthalene, afforded the title compound with the yield of 20%. $^1$H NMR (DMSO-d$_6$, 500 MHz): 7.85 (4H, m), 7.68 (2H, m), 7.47 (3H, m), 7.19 (1H, t, 5.8 Hz), 6.70 (1H, s), 6.66 (2H, m), 4.49 (2H, d, 5.8 Hz), 2.21 (6H, s); MS (ESI$^+$): m/z 441 (M+H)$^+$.

Example 21
N-(4,6-Dimethylpyrimidin-2yl-)4(3-methoxybenzylamino)-benzenesulfonamide (Compound E)

Following the procedure outlined in example 11, but substituting benzyl bromide by 3-methoxybenzyl bromide, afforded the title compound with the yield of 28%. $^1$H NMR (CDCl$_3$, 500 MHz): 7.93 (2H, m), 6.86 (3H, m), 6.58 (3H, m), 4.33 (2H, s), 3.78 (3H, s), 2.33 (6H, s); MS (ESI$^+$): m/z 421 (M+Na)$^+$, 399 (M+H)$^+$.

Example 22
N-(4,6-Dimethylpyrimidin-2-yl)-4-(4-nitrobenzylamino)-benzenesulfonamide Following the procedure outlined in example 11, but substituting benzyl bromide by 4-nitrobenzyl bromide, afforded the title compound with a yield lower than 1%. MS (ESI$^+$): m/z 414 (M+H)$^+$.

Example 23
N-(4,6-Dimethylpyrimimidin-2-yl)-4-(4-trifluoromethylbenzylamino)-benzenesulfonamide Following the procedure outlined in example 11, but substituting benzyl bromide by 4-trifluoromethylbenzyl bromide, afforded the title compound in a yield similar to that described in example 1 for step III. MS (ESI$^+$): m/z 459 (M+Na)$^+$, 437 (M+H)$^+$.

Example 24
4-[Bis-(4-trifluoromethylbenzyl)-amino]-N-(4,6-dimethylpyrimidin-2-yl)-benzenesulfonamide Title compound was purified from the reaction mixture produced according to example 23 with the yield of 20%. MS (ESI$^+$): 617 m/z (M+Na)$^+$, 595 (M+H)$^+$.

Example 25
N-(4,6-Dimethylpyrimimidin-2-yl)-4-(4-trifluoromethylbenzylamino)-benzenesulfonamide Following the procedure outlined in example 11, but substituting benzyl bromide by 4-trifluoromethoxybenzyl bromide, afforded the title compound with a yield of 25%. MS (ESI$^+$); m/z 475 (M+Na)$^+$, 453 (M+H)$^+$.

Example 26
4-[Bis-(4-trifluoromethoxybenzyl)-amino]-N-(4,6-dimethylpyrimidin-2-yl)-benzenesulfonamide Title compound was purified from the reaction mixture produced according to example 25 with a yield of 15%. MS (ESI$^+$): m/z 649 (M+Na)$^+$, 627 (M+H)$^+$.

Example 27
4-(2,5-Dimethylbenzylamino)-N-(4,6dimethylpyrimidin-2-yl)-benzenesulfonamide Following the procedure outlined in example 11 without caesium carbonate and substituting benzyl bromide by 2,5-dimethylbenzyl bromide afforded the title compound with a yield of 35%. $^1$H NMR (CDCl$_3$, 500 MHz): 7.93 (2H, m), 7.07 (3H, m), 6.59 (3H, m), 4.25 (2H, s), 2.33 (6H, s), 2.30 (3H, s), 2.28 (3H, s); MS (ESI$^+$): m/z 419 (M+Na)$^+$.

Example 28
4-(2,6-Dimethylbenzylamino)-N-(4,6dimethylpyrimidin-2-yl)-benzenesulfonamide Following the procedure outlined in example 11 without caesium carbonate and substituting benzyl bromide by 2,6-dimethylbenzyl bromide afforded the title compound with a yield of 25%. $^1$H NMR (CDCl$_3$, 500 MHz): 7.99 (2H, m), 7.08 (3H, m), 6.62 (3H, m), 4.26 (2H, s,), 2.37 (12H, m); MS (ESI$^+$): m/z 419 (M+Na)$^+$.

Example 29
4-(3,5-Dimethylbenzylamino)-N-(4,6dimethylpyrimidin-2-yl)-benzenesulfonamide Following the procedure outlined in example 11 without caesium carbonate and substituting benzyl bromide by 3,5-dimethoxybenzyl chloride afforded the title compound with a yield of 15%. $^1$H NMR (CDCl$_3$, 500 MHz): 7.92 (2H, m), 6.60 (1H, s), 6.58(2H, m), 6.46 (2H, m), 6.38 (1H, m), 4.30 (2H, s), 3.76 (6H, s), 2.33 (6H, s); MS (ESI$^+$): m/z 429 (M+H)$^+$.

Example 30
4-(2,5-Dimethylbenzylamino)-N-(4,6dimethylpyrimidin-2-yl)-benzenesulfonamide Following the procedure outlined in example 11 without caesium carbonate and substituting benzyl bromide by 2,5-inethoxybenzyl chloride afforded the title compound with the yield of 13%. Reaction time was three days. $^1$H NMR (CDCl$_3$, 500 MHz): 7.91 (2H, m), 6.79 (3H, m), 6.58 (3H, m), 4.33 (2H, s), 3.81 (3H, s), 3.71 (3H, s), 2.33 (6H, s); MS (ESI$^+$): m/z 429 (M+H)$^+$. Image Page 11

Example 31
2,6-Dichloro-N-[4-(4,6-dimethylpyrimidin-2-ylsufamoyl)-phenyl]-benzamide Following the procedure outlined in example 11, but substituting benzyl bromide by 2,6-dichlorobenzoyl chloride, afforded the title compound with almost quantitative yield. $^1$H NMR (CDCl$_3$, 500 MHz): 8.11 (2H, m), 7.80 (2H, m), 7.33 (3H, m), 6.59 (1H, s), 2.34 (6H, s); MS (ESI$^+$): m/z 473 (M+H)$^+$, 451 (M+H)$^+$.

Example 32
4-(2-Cyanobenzylamino)-N-(4,6-dimethylpyrimidin-2yl)-benzenesulfonamide Following the procedure outlined in example 11, but substituting benzyl bromide by α-bromo-o-tolunitrile, afforded the title compound with a yield of 21%. $^1$H NMR (DMSO-d$_6$, 500 MHz): 7.83 (1H, m), 7.71 (2H, m), 7.65 (1H, m), 7.47 (2H, m), 7.15 (1H, br, t, 5.8 Hz), 6.73 (1H, m), 6.63 (2H, m), 4.50 (2H, d, 5.8 Hz), 2.24 (6H, s); MS (ESI$^+$): m/z 416 (M+Na)$^+$, 394 (M+H)$^+$.

Example 33
4-(2,4-Dimethoxybenzylamino)-N-(4,6-dimethylpyrimidin-2-yl)-benzenesulfonamide 62 mg (0.37 mmol) 2,4-dimethoxybenzylaldehyde and 100.9 mg (0.36 mmol) sulfamethazine were dissolved in 4 ml of 1,2-dichloroethane. Acetic acid (168 μl, 2.8 mmol) was added to the reaction mixture and solution was stirred with reflux overnight. Sodium triacetoxyborohydride (162.9 mg, 0.77 mmol) was dissolved to the reaction solution and refluxing was continued for three hours. The reaction mixture was then evaporated to dryness, and purified on silica using gradient elution (chloroform to 2% methanol in chloroform) and 2:1 petrol ether:ethylacetate to obtain the title compound as white crystals with a yield of 10%. $^1$H NMR (CDCl$_3$, 500 MHz): 7.91 (2H, m), 7.13 (1H, m), 6.58 (3H, m), 6.47 (1H, m), 6.42 (1H, m), 4.53 (1H, t, 5.0 Hz), 4.30 (2H, d, 5.0 Hz), 3.82 (3H, s), 3.79 (3H, s), 2.33 (6H, s); MS (ESI$^+$): m/z 429 (M+H)$^+$.

Example 34
N-(4,6-Dimethylpyrimidin-2-yl)-4-[(1-ethyl-1H-indol-3-ylmethyl)-amino]-benzenesulfonamide (Compound F)

1-ethylindole-3-carboxaldehyde was prepared from alkylation reaction of indole-3-carboxaldehyde. Indole-3-carboxaldehyde (900 mg, 6.2 mmol) was dissolved in 5 ml dimethylformamide, ethyl bromide (918 μl, 12 mmol) and sodium hydride (282.8 mg, 12 mmol) were added to the reaction mixture. Solution was stirred and refluxed for three hours. The reaction mixture was then evaporated to dryness and washed with water. Pale brown crystals were obtained with 80% yield.

Following the procedure outlined in example 33, but substituting 2,4-dimethoxybenzylaldehyde by 1-ethylindole-3-carboxaldehyde, afforded the title compound with a yield similar to that of 4-(2,4-dimethoxybenzylaflUflo)-N-(4,6-dimethylpyrimidin-2-yl)-benzeenesulfonamide. Instead of sodium triacetoxyborohydride sodium borohydride was used to reduce the imine intermediate. $^1$H NMR (CDCl$_3$, 500 MHz): 7.88 (2H, m), 7.52 (1H, m), 7.29 (1H, m), 7.18 (1H, m), 7.05 (1H, m), 7.03 (1H, s), 6.56 (2H, m), 6.52 (1H, s), 4.41 (2H, d, 4.7 Hz), 4.33 (1H, t, 4.7 Hz), 4.08 (2H, q, 7.3 Hz), 2.27 (6H, s), 1.38 (3H, t, 7.3 Hz); MS (ESI$^+$): m/z 458 (M+Na)$^+$.

Example 35
N-[4-(4,6-Dimethylpyrimidin-2-ylsulfamoyl)-phenyl]-2-(2-methoxyphenyl)-acetamide 2-Methoxyphenylacetic acid (33 mg, 0.20 mmol) and sulfamethazine (55 mg, 0.20 mmol) were dissolved in 4 ml of chloroform. Triethylamine (70 μl, 0.55 mmol) and diisopropylcarbodiimide (50 μl, 0.20 mmol) were added to the reaction mixture. Solution was stirred and refluxed overnight. The reaction mixture was then evaporated to dryness, washed with water and purified on silica using gradient elution (chloroform to 2% methanol in chloroform) to obtain white crystals with the yield of 40%. $^1$H NMR (CDCl$_3$, 500 MHz): 8.04 (2H, m), 7.54 (2H, m), 7.30 (2H, m), 6.98 (2H, m), 6.60 (1H, s), 3.95 (3H, s), 3.72 (2H, s), 2.33 (6H, s); MS (ESI$^+$): m/z 449 (M+Na)$^+$, 427 (M+H)$^+$.

Example 36
2-Acetyl-N-[4-(4,6-dimethylpyrimidin-2-ylsulfamoyl)-phenyl]-benzamide Following the procedure outlined in example 35, but substituting 2-methoxyphenylacetic acid by 2-acetylbenzoic acid, afforded the title compound with a yield of 11%. MS (ESI$^+$): m/z 447 (M+Na)$^+$, 425 (M+H)$^+$.

Example 37
1-Methyl-1H-indole-2-carboxylic acid [4-(4,6-dimethylpyrimidin-2-ylsulfaoy)-phenyl]-amide Following the procedure outlined in example 35, but substituting 2-methoxyphenylacetic acid by 1-methylindole-2-carboxylic acid and using dimethylformamide as a solvent afforded the title compound with a yield similar to that of N-[4-(4,6-dimethylpyrimidin-2-ylsulfamoyl)-phenyl]-2-(2-methoxyphenyl)acetamide. MS (ESI$^+$): m/z 458 (M+Na)$^+$.

Example 38
2-(3,5-Dimethoxyphenyl)-N-[4-(4,6-dimethylpyrimidin-2-ylsufamoyl)-phenyl]-acetamide Following the procedure outlined in example 35, but substituting 2-methoxyphenylacetic acid by 3,5-dimethoxyphenylacetic acid, afforded the title compound with a yield of 54%. MS (ESI$^+$): m/z 457 (M+H)$^+$.

Example 39
N-(4,6-Dimethylpyrimidin-2-yl)-4-[2-(2-methoxyphenyl)-ethylamino]-benzenesulfonamide (Compound G)

33 mg (0.08 mmol) N-[4-(4,6-dimethylpyrimidin-2-ylsulfomoyl)-phenyl]-2-(2-methoxyphenyl)-acetamide was dissolved in 2 ml tetrahydrofurane. 340 µl of 1 M borane tetrahydrofurane complex was added to the reaction mixture under nitrogen atmosphere and solution was stirred overnight with reflux. Reaction was quenched with 6 M HCl and the reaction mixture was neutralised with 1 M NaOH. Product was extracted with chloroform and purified on silica using gradient elution (chloroform to 2% methanol in chloroform) to obtain white crystals with a yield of 20%. $^1$H NMR (CDCl$_3$, 500 MHz): 7.92 (2H, m), 7.22 (1H, m), 7.12 (1H, m), 6.89 (2H, m), 6.60 (1H, br, s), 6.54 (2H, m), 3.85 (3H, s), 3.38 (2H, t, 6.9 Hz), 2.93 (2H, t, 6.9 Hz), 2.33 (6H, s); MS (ESI$^+$): m/z 435 (M+Na)$^+$, 413 (M+H)$^+$.

Example 40
4-[2-(3,5-Dimethoxyphenyl)-ethylamino]-N-(4,6dimethylpyrimidin2yl)-benzenesulfonamide Following the procedure outlined in example 39, but substituting N-[4-(4,6-dimethylpyrimidin-2-ylsufamoyl)-phenyl)-phenyl]-2-(2-methoxyphenyl)-acetamide by 2-(3,5-dimethoxyphenyl) -N-[4-(4,6-dimethylpyrimidin-2ylsulfamoyl)-phenyl]-acetamide, afforded the title compound with a yield of 11%. $^1$H NMR (CDCl$_3$, 500 MHz): 7.92 (2H, m), 6.58 (1H, s), 6.54 (2H, m), 6.34 (3H, s), 4.20 (1H, t, 5.8 Hz), 3.76 (6H, s), 3.42 (2H, m), 2,85 (2H, t, 6.9 Hz), 2.34 (6H, s); MS (ESI$^+$): m/z 465 (M+Na)$^+$, 443 (M+H)$^+$.

Example 41
4-(Benzhydrylamino)-N-(4,6-dimethylpyrimidin-2-yl)-benzenesulfonamide (Compound H)

Sulfamethazine (105 mg, 0.38 mmol) and diphenylchloromethane (77 µl, 0.38 mmol) were dissolved in 3 ml pyridine. Solution was stirred and refluxed overnight. The reaction mixture was evaporated to dryness and dissolved to 1 M NaOH. Product was precipitated with 1 M acetic acid. Precipitation cycle was repeated for three times to give white crystals of the title compound with a yield of 8%. MS (ESI$^+$): m/z 467(M+Na)$^+$, 445 (M+H)$^+$.

Example 42
4-(4-Aminobenzylamino)-N-(4,6-dimethylpyrimidin-2-yl)-benzenesulfonamide 18 mg (0.04 mmol) of N-(4,6-dimethylpyrimidin-2-yl)-4-(4-nitrobenzylamino)-benzenesulfonamide was dissolved in 1 ml of tetrahydrofurane. Hydrazinium hydrate (50 µl, 1.5 mmol) and catalytic amount of palladium on charcoal were added to the reaction mixture. Solution was stirred overnight. The reaction mixture was evaporated to dryness and purified on silica using gradient elution (chloroform to 4% methanol in chloroform) to obtain with a yield of 59%. MS (ESI$^+$): m/z 406 (M+H)$^+$, 384 (M+H)$^+$.

Example 43
4-{[4-(4,6-Dimethylpyrimidin-2-ylsulfamoyl)-phenylamino]-methyl}-benzamide 4-{[4-(4,6-Dimethylpyrimidin-2-ylsulfamoyl)-phenylamino]-methyl}-benzoic acid methyl ester was prepared like described on example 11 and was treated with 25% ammonia to obtain the title compound with a yield lower than 1%. $^1$H NMR (CDCl$_3$, 500 MHz): 7.81 (2H, m), 7.67 (2H, m), 7.37 (2H, m), 7.12 (1H, br, t, 6.0 Hz), 6.72 (1H, s), 6.60 (2H, m), 4.37 (2H, d, 6.0 Hz), 2.33 (6H, s); MS (ESI$^+$): m/z 412 (M+H)$^+$.

Example 44
4-{[(2,6-Dichloro-phenyl)-hydroxy-methyl]-amino}-N-(4,6-dimethyl-pyrimidin-2-yl)-benzenesulfonamide 11 mg (0.02 mmol) of 2,6-dichloro-N-[4-(4,6-dimethylpyrimidin-2-yl-sulfamoyl)-phenyl]-benzamide was dissolved in 2 ml tetrahydrofurane. Lithium aluminium hydride (6 mg, 0.16 mmol) was added to the reaction mixture under nitrogen atmosphere and solution was stirred overnight. The reaction mixture was filtered, evaporated to dryness and purified by on silica using gradient elution (chloroform to 4% methanol in chloroform) to obtain the title compound with a yield of 18%. MS (ESI$^+$): m/z 475 (M+Na)$^+$.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Cheng, Y., and Prusoff, W. H., 1973. Biochem. Pharmacol. 22: 3099

Jasper, J. R., Lesnick, J. D., Chang, L. K., Yamanashi, S. S., Chang, T. C., Hsu, S. A. O., Daunt, D. A., Bonhaus, D. W., and Egen, R. M., 1998. Biochem. Pharmacol. 55: 1035

Marjamäki, A., Ala-Uotila, S., Luomala, K., Perälä, M., Jansson, C., Jalkanen, M., Regan, J. W., and Scheinin, M., 1992. Biochem. Biophys. Acta 1134: 169

Marjamäki, A., Pihlavisto, M., Cockcroft, V., Heinonen, P., Savola, J.-M., and Scheinin, M., 1998. Mol. Pharmacol. 53: 370

Pohjanoksa, K., Jansson, C. C., Luomala, K., Marjamäki, A., Savola, J.-M., and Scheinin, M., 1997. Eur. J. Pharmacol. 35: 53

Tian, W.-N., Duzic, E., Lanier, S. M., and Deth, R. C., 1993. Mol. Pharmacol. 45: 524

Kumar, V. B., Reddy, M. V., Indian J. Chem., Sect. B (1985), 24B(12), 1298–1301

Farag, A. M., El-Mouafi, H. M., Khalifa, M., 1991. Egypt. J. Pharm. Sci. 32 (3–4), 951–9

Wieland, T., and Jakobs, K. H., 1994. Meth. Enzymol. 237: 3

Heinonen et al. 1999, The Journal of Clinical Endocrinology & Metabolism, 84:2429

Link R E et al., 1996, Science 273:803

MacMillan L B et al., 1996, Science 273:801

What is claimed is:

1. A compound of formula (I)

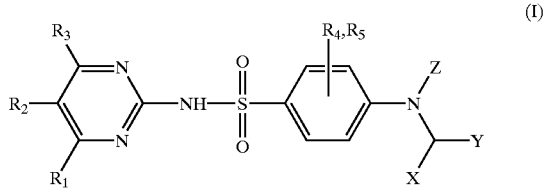

or a pharmaceutically acceptable salt thereof wherein $R_1$, $R_2$, $R_3$, $R_4$ and $R_5$ are independently of each other H, a straight or branched alkyl or alkoxy group with 1 to 4 carbon atoms, or a halogen;

X is H, a straight or branched alkyl chain having 1 to 4 carbon atoms, phenyl or —OH;

Z is H, acetyl, —CH$_2$—Ph—O—CF$_3$ or —CH$_2$—Ph—CF$_3$, where Ph is phenyl;

Y is a ring structure optionally linked to formula (I) with an alkyl chain having one or two carbon atoms, wherein the ring structure is a) phenyl optionally mono- or disubstituted, wherein each substituent is independently selected from the group consisting of a halogen, a straight or branched alkyl or alkoxy chain with 1 to 4 carbon atoms, a halogen substituted methyl or methoxy group, a nitrile group, an amide group, an amino group, and a nitro group;

b) 2-benzimidazolyl, 2-imidazolyl, or 2- or 3-indolyl, wherein one N optionally has a substituent that is a straight or branched alkyl or alkoxy chain with 1 to 4 carbon atoms, or benzyl; and wherein the 2-benzimidazolyl, 2-imidazolyl, or 2- or 3-indolyl is optionally mono- or disubstituted, wherein each substituent is independently a straight or branched alkyl or alkoxy group with 1 to 4 carbon atoms, or a halogen;

(c) pyridinyl optionally mono- or disubstituted, wherein each substituent is independently a straight or branched alkyl or alkoxy group with 1 to 4 carbon atoms, or a halogen; or (d) naphthyl optionally mono- or disubstituted, wherein each substituent is independently a straight or branched alkyl or alkoxy group with 1 to 4 carbon atoms, or a halogen;

provided that if $R_1$ is methyl; and $R_2$, $R_4$, $R_5$, Z and X is H;

then Y cannot be an unsubstituted 2-benzimidazolyl if $R_3$ is methyl or H, nor can Y be a monosubstituted 2-benzimidazolyl wherein one N has a methyl or ethyl substitution if $R_3$ is methyl, and provided that the compound of formula 1 cannot be N-(4-methyl-2-pyrimidinyl)-4-[[(1-methyl-1H-benzimidazol-2-yl)methyl]amino-benzene.

2. The compound of claim 1, wherein $R_1$ and $R_3$ are methyl and $R_2$, $R_4$ and $R_5$ are H.

3. The compound of claim 1, wherein X is H, Y is a phenyl optionally mono- or disubstituted with a straight or branched alkoxy group and Z is H.

4. The compound of claim 1, wherein said phenyl is substituted and said alkoxy substituent is methoxy and said compound is selected from the group consisting of 4-(2,4-dimethoxybenzylamino)-N-(4, 6-dimethylpyrimidin-2yl)-benzenesulfonamide, N-(4, 6-dimethylpyrimidin-2-yl)-4-(3-methoxybenzylamino)-benzenesulfonamide, 4-(3,5-dimethoxbenzylamino)-N-(4,6-dimethylpyrimidin-2-yl)-benzenesulfonamide, 4-(2,5-dimethoxybenzylamino)-N-(4,6-dimethylpyrimidin-2-yl)-benzenesulfonamide and N-(4,6-dimethylpyrimidin-2yl)-4-(2methoxybenzylamino)-benzenesulfonamide.

5. The compound of claim 1, wherein X is H, Y is a phenyl optionally mono- or disubstituted with a straight or branched alkyl and/or a halogen and Z is H.

6. The compound of claim 1, wherein said compound is selected from the group consisting of 4-benzylamino-N-(4, 6-dimethylpyrimidin-2-yl)-benzenesulfonamide, N-(4,6-dimethylpyrimidin-2-yl)-4-(2-methylbenzylamino)-benzenesulfonamide, 4-(2,4-dimethylbenzylamino)-N-(4,6-dimethylpyrimidin-2-yl)-benzenesulfonamide, N-(4,6-dimethylpyrimidin-2-yl)-4-(3-methylbenzylamino)-benzenesulfonamide, N-(4,6-dimethylpyrimidin-2-yl)-4-(4-methylbenzylamino)-benzenesulfonamide, 4-(2,5-dimethylbenzylamino)-N-(4,6-dimethylpyrimidin-2-yl)-benzenesulfonamide, 4-(2,6-dimethylbenzylamino)-N-(4,6-dimethylpyrimidin-2-yl)-benzenesulfonamide, 4-4-bromobenzylamino)-N-(4,6-dimethylpyrimidin-2-yl)-benzenesulfonamide and 4-(2,6-dichlorobenzylamino)-N-(4,6dimethylpyrimidin-2-yl)-benzenesulfonamide.

7. The compound of claim 2, selected from the group consisting of N-(4,6-dimethylpyrimidin-2-yl)-4-[(1-ethyl-1H-indol-3-ylmethyl)-amino]-benzenesulfonamide, N-(4,6-dimethylpyrimidin-2-yl-4-[(1-isobutyl-1H-benzimidazol-2-ylmethyl)-amino]-benzenesulfonamide, N-(4,6-dimethylpyrimidin-2-yl)-4-(1-phenylethylamino)-benzenesulfonamide, N-(4,6-dimethylpyrimidin-2-yl)-4-[2-(2-methoxyphenyl)-ethylamino]-benzenesulfonamide and N-(4,6-dimethylpyrimidin-2-yl)-4-[(naphthalen-2-ylmethyl)-amino]-benzenesulfonamide.

8. A method for the treatment or prevention of a disease mediated by the alpha-2B-adrenoceptor in a mammal, comprising administering an alpha-2B-adrenoceptor antagonist to a mammal in need of said treatment, said antagonist comprising a compound of formula (I)

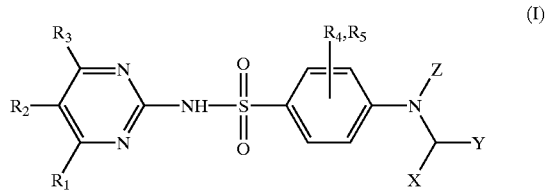

or a pharmaceutically acceptable salt thereof wherein $R_1$, $R_2$, $R_3$, $R_4$ and $R_5$ are independently of each other H, a straight or branched alkyl or alkoxy group with 1 to 4 carbon atoms, or a halogen;

X is H, a straight or branched alkyl chain having 1 to 4 carbon atoms, phenyl or —OH or =O;

Z is H, acetyl, —CH$_2$—Ph—O—CF$_3$ or —CH$_2$—Ph—CF$_3$, where Ph is phenyl;

Y is a ring structure optionally linked to formula (I) with an alkyl chain having one or two carbon atoms, wherein the ring structure is a) phenyl optionally mono- or disubstituted, wherein each substituent is independently selected from the group consisting of a halogen, a straight or branched alkyl or alkoxy chain with 1 to 4 carbon atoms, a halogen substituted methyl or methoxy group, an acetyl group, a nitrile group, an amide group, an amino group, or a nitro group;

b) 2-benzimidazolyl, 2-imidazolyl, or 2- or 3-indolyl, wherein one N optionally has a substituent that is a straight or branched alkyl or alkoxy chain with 1 to 4 carbon atoms, or benzyl; and wherein the 2-benzimidazolyl, 2-imidazolyl or 2- or 3-indolyl is optionally mono- or disubstituted, wherein each substituent is independently a straight or branched alkyl or alkoxy group having 1 to 4 carbon atoms, or a halogen;

(c) pyridinyl optionally mono- or disubstituted, wherein each substituent is independently a straight or branched alkyl or alkoxy group with 1 to 4 carbon atoms, or a halogen; or (d) naphthyl optionally mono- or disubstituted, wherein each substituent is independently a straight or branched alkyl or alkoxy group with 1 to 4 carbon atoms, or a halogen;

provided that if R$_1$ and R$_3$ is methyl; and R$_2$, R$_4$, R$_5$, Z and X is H; then Y cannot be a monosubstituted 2-benzimidazolyl wherein one N has a methyl or ethyl substitution; or if R$_1$ and R$_3$, is methyl; R$^2$, R$_4$, R$_5$ and Z is H and X is =O;

then Y cannot be a monosubstituted phenyl with an ethoxy group in the 4-position, and wherein said disease relates to obesity or a low basal metabolic rate, or is a vascular disease selected from the group consisting of coronary heart disease, acute myocardial infarction, all forms of angina and essential hypertension.

9. The method of claim 8, wherein R$_1$ and R$_3$ are methyl and R$_2$, R$_4$ and R$_5$ are H.

10. The method of claim 8, wherein X is H, Y is a phenyl optionally mono- or disubstituted with a straight or branched alkoxy group and Z is H.

11. The method of claim 8, wherein said phenyl is substituted and said alkoxy substituent is methoxy, and said compound is selected from the group consisting of 4-(2,4-dimethoxybenzylamino)-N-(4,6dimethylpyrimidin-2-yl)-benzenesulfonamide, N-(4,6-dimethylpyrimidin-2-yl)-4-(3-methoxybenzylamino)-benzenesulfonamide, 4-(3,5-dimethoxybenzylamino)-N-(4,6-dimethylpyrimidin-2-yl)-benzenesulfonamide, 4-(2,5-dimethoxybenzylamino)-N-(4,6-dimethylpyrimidin-2-yl)-benzenesulfonamide and N-(4,6-dimethylpyrimidin-2-yl)-4-(2methoxybenzylamino)-benzenesulfonamide.

12. The method of claim 8, wherein X is H, Y is a phenyl optionally mono- or disubstituted with a straight or branched alkyl and/or a halogen, and Z is H.

13. The method of claim 8, wherein said compound is selected from the group consisting of 4-benzylamino-N-(4,6-dimethylpyrimidin-2-yl)-benzenesulfonamide, N-(4,6-dimethylpyrimidin-2-yl)-4-(2-methylbenzylamino)-benzenesulfonamide, 4-(2,4-dimethylbenzylamino)-N-(4,6-dimethylpyrimidin-2-yl)-benzenesulfonamide, N-(4,6-dimethylpyrimidin-2-yl)-4-(3-methylbenzylamino)-benzenesulfonamide, N-(4,6-dimethylpyrimidin-2-yl)-4-(4-methylbenzylamino)-benzenesulfonamide, 4-(2,5-dimethylbenzylamino)-N-(4,6-dimethylpyrimidin-2-yl)-benzenesulfonamide, 4-(2,6-dimethylbenzylamino)-N-(4,6-dimethylpyrimidin-2-yl)-benzenesulfonamide, 4-(4-bromobenzylamino)-N-(4,6-dimethylpyrimidin-2-yl)-benzenesulfonamide and 4-(2,6-dichlorobenzylamino)-N-(4,6-dimethylpyrimidin-2-yl)-benzenesulfonamide.

14. The method of claim 9, wherein said compound is selected from the group consisting of 4-[(1H-benzimidazol-2-ylmethyl)-amino]-N-(4,6-dimethylpyrimidin-2-yl)-benzenesulfonamide, N-(4,6-dimethylpyrimidin-2-yl)-4-[(1-ethyl-1H-indol-3-ylmethyl)-amino]-benzenesulfonamide, N-(4,6-dimethylpyrimidin-2-yl)-4-[(1-isobutyl-1H-benzimidazol2-ylmethyl)-amino]-benzenesulfonamide, N-(4,6-dimethylpyrimidin-2-yl)-4-(1phenylethylamino)-benzenesulfonamide, N-(4,6-dimethylpyrimidin-2-yl)-4-(1-phenylethylamino)-methoxyphenyl)-ethylamino]-benzenesulfonamide and N-(4,6-dimethylpyrimidin-2-yl)-4-[(naphthalen-2-ylmethyl)-amino]-benzenesulfonamide.

15. The method of claim 8, wherein the disease is a coronary heart disease (CHD).

16. The method of claim 8, wherein the disease is selected from the group consisting of acute myocardial infarction (AMI), unstable angina pectoris, Prinzmetal's variant form of angina pectoris, other forms of chronic angina pectoris and CHD, and restenosis after coronary angioplasty.

17. The method of claim 8, wherein the disease is essential hypertension.

18. The method of claim 8, wherein the disease is a vascular disesase selected from the group consisting of vasoconstriction obesity.

19. The method of claim 8, wherein said mammal is an individual having a deletion of 3 glutamates from the glutamic acid repeat element of 12 glutamates (amino acids 297–309), in an acid stretch of 17 amino acids, located in the third intracellular loop of the receptor polypeptide.

20. The method of claim 19, wherein said individual is a deletion/deletion genotype.

21. A method for potentiating the clinical efficiency of an anaesthetic and/or analgetic alpha-2-adrenoceptor agonist, said agonist not being selective for the alpha-2B-adrenoceptor subtype, comprising administering a therapeutically effective amount of the alpha-2-adrenoceptor antagonist of claim 1 to a mammal.

* * * * *

UNITED STATES PATENT AND TRADEMARK OFFICE
CERTIFICATE OF CORRECTION

PATENT NO. : 6,767,909 B2
DATED : July 27, 2004
INVENTOR(S) : Topi Joutsamo et al.

It is certified that error appears in the above-identified patent and that said Letters Patent is hereby corrected as shown below:

Title page,
Item [75], Inventors, change "Anna-Maria Hoffrén" to -- Anna-Marja Hoffrén --; and change "Siegfreid Wurster" to -- Siegfried Wurster --.
Item [56], References Cited, OTHER PUBLICATIONS,
"CA Registry, RN 354563-18-1," reference, change "Benzenesulfonamide, 4-[[(1-methyl-1H-benzimidazol-2yl)methyl]amino]-N-(4-methyl-2-pyrimidinyl)-" to -- Benzenesulfonamide, 4-[[(1-methyl-1H-benzimidazol-2-yl]methyl]amino-N-(4-methyl-2-pyrimidinyl)- --;
"STN International Chemcats AN 2002:1405436," reference, change "Benzenesulfonamide, 4[1(1-methyl-iH-benzimidazol-2-yl)methyl]-N-(4-methyl-2-pyrimidinyl)-" to -- Benzenesulfonamide, 4-[[1-methyl-1H-benzimidazol-2-yl]methyl]amino-N-(4-methyl-2-pyrimidinyl)- --;
"Heinonen et al.," reference, after "metabolic" delete -- acid --.
Item [57], ABSTRTACT,
Line 2, change "antagoist" to -- antagonist --.

Column 7, line 52 through Column 8, line 8,
Relocate "Experimental Section" ending with the words "three times.", to Column 7, line 15.

Column 7,
Between lines 33 and 34, insert a space.

Column 9,
Line 58, change "DMSOd$_6$" to -- DMSO-d$_6$ --;
Line 67, change "5-methoxysulfadiazifle" to -- 5-methoxysulfadizine --

Column 10,
Lines 1-2, change "Dimethylformaiflide" to -- Dimethylformamide --.

Column 11,
Lines 59-60, change "(4,6dimethylpyrimidin-2-yl)" to -- (4,6-dimethylpyrimidin-2-yl) --.

UNITED STATES PATENT AND TRADEMARK OFFICE
CERTIFICATE OF CORRECTION

PATENT NO.    : 6,767,909 B2
DATED         : July 27, 2004
INVENTOR(S)   : Ropi Joutsamo et al.

It is certified that error appears in the above-identified patent and that said Letters Patent is hereby corrected as shown below:

Column 12,
Line 13, change "(2,6Dichlorobenzylamino)" to -- (2,6-Dichlorobenzylamino)--;
Line 34, change "(4,6-Dimethylpyrimidin-2yl-)4(3-methoxybenzylamino)" to -- (4,6-Dimethylprimidin-2yl-)-4-(3-methoxybenzylamino) --.

Column 13,
Lines 17, 27, 37 and 49, change "4,6dimethylpyrimidin" to -- 4,6-dimethylpyrimidin --;
Lines 52-53, change "2,5-inethoxybenzyl" to -- 2,5-methoxybenzyl --;
Line 57, delete "Image Page 11".

Column 14,
Lines 45-47, change "4-(2,4-dimethoxybenzylaflUflo)-N-(4,6-dimethylpyrimidin-2-yl)-benzeenesulfonamide" to -- 4-(2,4-dimethoxybenzylamino)-N-(4,6-dimethylpyrimidin-2-yl)-benzenesulfonamide --.

Column 15,
Line 14, change "dimethylpyrimidin-2-ylsulfaoy)" to -- dimethylpyrimidin-2-ylsulfamoyl) --.
Line 49, change "6dimethylpyrimidin2yl)" to -- 6-dimethylpyrimidin-2-yl) --.

Column 18,
Line 11, change "(4, 6-dimethylpyrimidin-2y1)" to -- (4,6-dimethylpyrimidin-2-yl) --;
Line 17, change "dimethylpyrimidin-2yl)-4-(2methoxybenzylamino)" to
-- dimethylpyrimidin-2-yl)-4-(2-methoxybenzylamino) --;
Line 36, change "(4,6dimethylpyrimidin-2-yl)" to -- (4,6-dimethylpyrimidin-2-yl) --;
Line 40, change "dimethylpyrimidin-2-yl" to -- dimethylpyrimidin-2-yl) --.

Column 19,
Line 31, insert a space between "Z" and "and";
Line 34 , after "$R_3$" delete "," (comma); and change "$R^2$" to -- $R_2$ --;
Line 51, change "4,6dimethylpyrimidin" to -- 4,6-dimethylpyrimidin --;
Line 57, change "2methoxybenzylamino" to -- 2-methoxybenzylamino --.

UNITED STATES PATENT AND TRADEMARK OFFICE
CERTIFICATE OF CORRECTION

PATENT NO. : 6,767,909 B2
DATED : July 27, 2004
INVENTOR(S) : Ropi Joutsamo et al.

It is certified that error appears in the above-identified patent and that said Letters Patent is hereby corrected as shown below:

Column 20,
Line 23, change "benzimidazol2" to -- benzimidazol-2 --;
Line 25, change "(1 phenylethylamino)" to -- (1-phenylethylamino) --;
Line 26, change "4-(1-phenylethylamino)" to -- 4-[2-(2- --;
Line 45, after "vasoconstriction" insert -- and --.

Signed and Sealed this

Twenty-first Day of December, 2004

JON W. DUDAS
*Director of the United States Patent and Trademark Office*